United States Patent [19]

Tait

[11] 3,939,404
[45] Feb. 17, 1976

[54] METHOD OF TESTING FOR AND PREVENTING THE POSSIBILITY OF CRACKING, SPALLING OR LIKE DEFECTS IN ROLLING MILL ROLLS BY DETERMINING THE RATE OF CHANGE IN HARDNESS

[75] Inventor: William H. Tait, Hamilton, Canada

[73] Assignee: Dominion Foundries and Steel, Limited, Hamilton, Canada

[22] Filed: July 10, 1974

[21] Appl. No.: 487,092

[52] U.S. Cl. .................................................. 324/40
[51] Int. Cl.² ........................................ G01R 33/12
[58] Field of Search............ 324/34 R, 34 H, 37, 40

[56] References Cited
UNITED STATES PATENTS

| | | | |
|---|---|---|---|
| 2,564,777 | 8/1951 | Cavanagh | 324/34 R |
| 2,673,613 | 3/1954 | Irwin | 324/34 R |
| 2,867,784 | 1/1959 | Shapiro | 324/34 R |
| 3,535,625 | 10/1970 | Pratt | 324/37 |

Primary Examiner—Robert J. Corcoran
Attorney, Agent, or Firm—Hirons & Rogers

[57] ABSTRACT

In a method of testing for and preventing the possibility of cracking, spalling or like defects in a rolling mill roll surface the surface is scanned to provide a representation of the hardness and/or the magnetic conductivity. The presence at a location of a rate of change of this characteristic of greater than a predetermined amount foreshadows the possibility of the occurrence of such a defect at this location. The roll is then subjected to an operation consisting of removal of the surface portion or heat treatment until the rate of change is below another predetermined amount. Preferably the method used to measure magnetic conductivity is eddy current testing. The removal operation may take place in steps until the rate of charge is below the another rate of charge.

13 Claims, 6 Drawing Figures

METHOD OF TESTING FOR AND PREVENTING THE POSSIBILITY OF CRACKING, SPALLING OR LIKE DEFECTS IN ROLLING MILL ROLLS BY DETERMINING THE RATE OF CHANGE IN HARDNESS

FIELD OF THE INVENTION

The present invention is concerned with a method of testing for and preventing the possibility of cracking, spalling or like defects in the rolls of a rolling mill.

Review of the Prior Art

A roll such as is used in a rolling mill constitutes a special example of a body having a surface that in use is subjected to intense mechanical forces. Such rolls are very expensive to manufacture and clearly it is desirable that they should have as long a working life as possible. A new roll has the maximum diameter usable in its mill housing and must be discarded after the diameter has been reduced to a specific minimum value. This reduction in diameter is inevitable owing to the need for periodic redressing and retruing of the cylindrical roll surface as it becomes worn and misshapen by the intense forces to which it is subjected.

It is well known that if stress is applied to a body surface of crystalline materials, particularly metals, the material adjacent to and including the surface becomes "work hardened" and embrittled. Thus, the stresses to which the rolls of a rolling mill are subjected during operation causes work hardening of the roll surface, with the possibility of fatigue and spalling of the metal. A "spall" or "spawl" is the name applied in the steel industry to a surface defect, wherein a metal segment separates from the roll surface to leave a corresponding shallow recess. A "shelf crack" is another form of defect wherein two adjacent segments of the roll appear to move radially relative to one another to form a crack bounded by a radially-protruding shelf. Such defects can only be eliminated by removal of the part of the roll periphery, including the defect, e.g. by cutting or grinding on a lathe, and the amount that must be removed is usually many times that required for normal re-dressing, and may be sufficient to prevent further use of the roll, considerably shortening the useful life of the rolls, e.g. by as much as 50%. The need for more frequent roll changes, and the production of marked rolled product when a roll spalls or cracks, also adversely affects the mill output.

The hardening that takes place with a rolling mill roll usually is found to occur in circular bands around the roll periphery, and usually (though not necessarily) is greatest towards its ends immediately adjacent the parts of the roll surface contacted by the edges of the strips that are rolled thereby. Eddy current conductivity testing is a well known non-destructive testing technique for obtaining an indication of the hardness of materials, since usually the magnetic conductivity of metals decreases as the hardness increases. It must be noted however that this particular method can be the subject of gross error, since some possible variables may affect the conductivity but not the hardness, and vice versa. The readings obtained with this particular non-destructive testing method are therefore qualitative and not quantitative.

Definition of the Invention

It is the principal object of the present invention to provide a method of testing for the possibility of cracking, spalling or like defects in the surface of a rolling mill roll.

It is also an object to provide a method of testing for and thereafter at least reducing the possibility of the occurrence of cracking, spalling or like defects in the surface of a rolling mill roll.

In accordance with the present invention there is provided a method of testing for and at least reducing the possibility of the occurrence of cracking, spalling or like defects in the exterior cylindrical surface of a cylindrical steel rolling mill roll, the method including the steps of:

a. determining the rate of change of hardness along a reference direction for at least a part of the roll surface to find locations therealong having rates of change greater than a predetermined maximum value known to foreshadow the possibility of the occurrence of defects for the roll and the conditions to which it is subjected in operation, and b. when the rate of change of hardness along the reference direction exceeds the said maximum value removing material from the roll including the tested surface until the rate of change of hardness is below another predetermined maximum value.

Also in accordance with the invention there is provided a method of testing for and at least reducing the possibility of the occurrence of cracking, spalling or like defects in the exterior cylindrical surface of a cylindrical steel rolling mill roll, the method including the steps of:

a. determining by means of an eddy current detector the rate of change of magnetic conductivity along a reference direction for at least a part of the roll surface to find locations therealong having rates of change greater than a predetermined maximum value known to foreshadow the possibility of the occurrence of defects for the roll and the conditions to which it is subjected in operation, and b. when the rate of change along the reference direction exceeds the said maximum value removing material from the roll including the tested surface until the rate of change is below another predetermined maximum value.

Further in accordance with the present invention there is provided a method of testing for and at least reducing the possibility of the occurrence of cracking, spalling or like defects in the exterior cylindrical surface of a cylindrical steel rolling mill roll, the method including the steps of:

a. determining the rate of change of hardness along a reference direction for at least a part of the roll surface to find locations therealong having rates of change greater than a predetermined maximum value known to foreshadow the possibility of the occurrence of defects for the roll and the conditions to which it is subjected in operation, and b. when the rate of change of hardness along the reference direction exceeds the said maximum value heat-treating the roll, c. determining the rate of change along the reference direction on the heat-treated roll, and d. repeating the steps b and c as necessary until the rate of change is below another prederermined maximum value.

Still further in accordance with the present invention there is provided a method of testing for and at least reducing the possibility of the occurrence of cracking, spalling or like defects in the exterior cylindrical surface of a cylindrical steel rolling mill roll, the method including the steps of:

a. determining by means of an eddy current detector the rate of change of magnetic conductivity along a reference direction for at least a part of the roll surface to find locations therealong having rates of change greater than a predetermined maximum value known to foreshadow the possibility of the occurrence of defects for the roll and the conditions to which it is subjected in operation, and b. when the rate of change along the reference direction exceeds the said maximum value heat-treating the roll, c. determining the rate of change along the reference direction on the heat-treated roll, and d. repeating the steps b and c as necessary until the rate of change is below another predetermined maximum value.

DESCRIPTION OF THE DRAWINGS

Particular preferred embodiments of the invention will now be described, by way of example, with reference to the accompanying diagrammatic drawings wherein.

DESCRIPTION OF THE PREFERRED EMBODIMENTS

Figure 1:
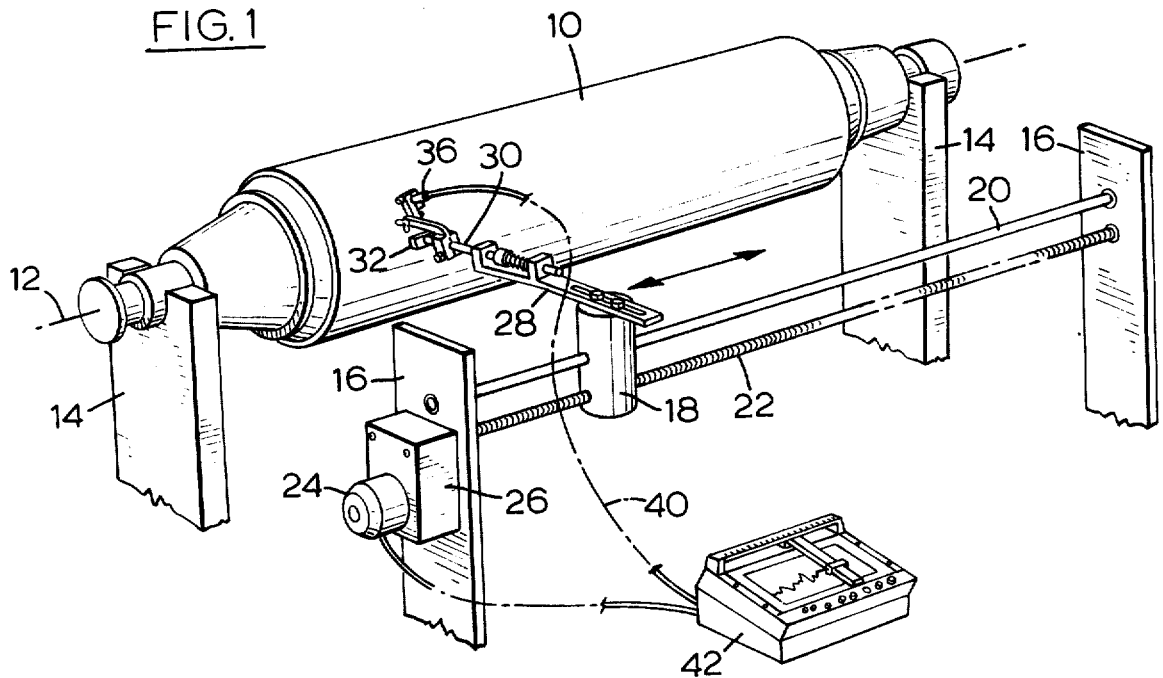
FIG. 1 is a perspective illustration of a steel roll for a rolling mill and showing also schematically apparatus used for measuring and producing a graphical representation of the surface hardness thereof.
Figure 2:
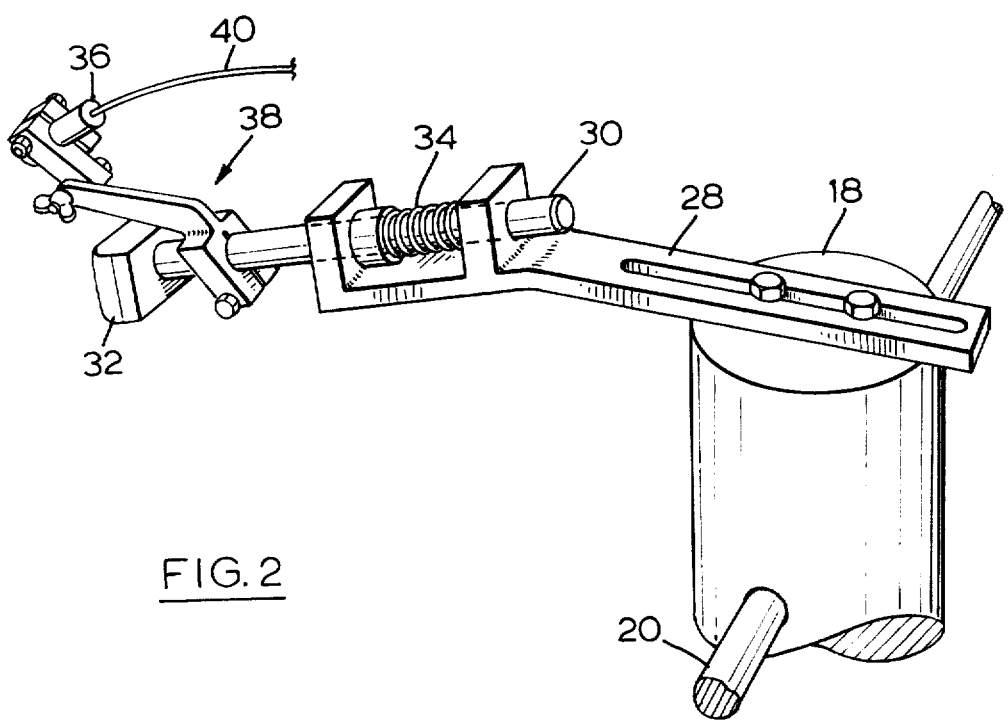
FIG. 2 is a perspective view of a detail of the apparatus of FIG. 1, drawn to a larger scale.

Referring now particularly to FIGS. 1 and 2 a roll 10 is illustrated schematically as being mounted for rotation about its axis 12 by means of upright standards 14, which are in turn mounted on a rigid base which is not shown. In view of the weight of the roll some mechanical means of turning it about its axis on the standards may be required, such as a grinder- or lathe-type drive of appropriate size.

Another pair of upright standards 16 mount a carriage 18 for movement parallel to the axis 12, the carriage sliding on a rod 20 extending between the standards and being driven in such sliding movement by a threaded rod 22, which is rotated by an electric motor 24 through a gear reduction box 26. An arm 28 is fastened securely to the carriage 18 and has at one end a slidably mounted rod 30, which carries at one end a bearing pad 32, and is urged by a spring 34 in the direction to press the pad against the roll periphery. An eddy current detection device 36 is mounted by a suitable adjustment assembly 38 on the end of the rod 30 and is adjusted in position thereon, so that the pad 32 just maintains it in sufficient contact with the roll periphery as it is scanned over that periphery. Other types of traversing mountings for the same purpose, such as the cross-feed table of a grinder or lathe in which the roll is mounted, will be apparent to those skilled in the art.

The detection device 36 is connected as by a cable 40 to a combined eddy current tester and chart recorder 42, the motor 24 being controlled in known manner via the recorder portion of the apparatus so that the plot or graph drawn by the device 36 corresponds to a scan across the full width of the roll 10, the device thereby producing directly plots or graphs such as those shown in FIGS. 3 to 6.

I have discovered that the possibility of a metal roll surface developing a defect, such as a crack or spall, upon the application thereto of mechanical forces it will encounter in normal operation, can be predicted with high accuracy by the use of the methods of the present invention.

In the preferred manner of operation a non-destructive testing method is used to obtain information that will correspond directly to, or be representative of, certain physical parameters of the material of the body as measured at and immediately adjacent the surface along a suitable reference direction. Any part of the surface along the reference line which has a rate of change of these parameters of greater than a predetermined maximum amount, for the particular material and the particular testing conditions to which it is subjected, is found to have a high probability as the potential site for the occurrence of a defect, such as a spall or crack. Once having found such a potential site then appropriate action can be taken to reduce the rate of change to below the said predetermined maximum level.

It is known at the present time that the rate of change of hardness is the principal physical parameter to be considered, but others are also believed to be involved such as crystal lattice distortion and dislocations and effective differences in heat treatment.

This invention has been applied to date to the testing of back-up rolls for a hot rolling mill in order to predict the possibility of them becoming defective in use by reason of cracking or spalling. It has been found possible by application of the invention to take action which will substantially reduce, even if it will not completely eliminate, the possibility of such defects occurring in the future use of the rolls. It has also been used very successfully to provide a specification for new rolls which are pre-tested before being put into operation, suitable preventative action being taken if the testing step shows a rate of change of hardness of more than the said maximum amount. The testing step can be applied at any time during the operation of the mill, and conveniently it is routinely applied when the rolls have been removed for re-truing.

Such a roll is a specific example of a body having a surface that in normal usage is subjected to high mechanical forces, and typically has a width of 66 inches and a diameter when new of 52.5 inches. These particular rolls are discarded when in normal operation their diameter has been reduced by wear and repeated redressing to 48.5 inches. Minor spalls are usually removed by grinding while larger spalls and cracks usually require recutting of the roll on a lathe and, if sufficiently deep, may result in the complete discard of the roll for further use. The invention may also be employed for the accurate determination when required of the depth of grind or cut that is necessary to reduce the possibility of defects in a roll predicted to become defective and, in the case of a defective roll, for complete elimination of the defect and prevention, as far as possible, of its recurrence.

Figure 3:
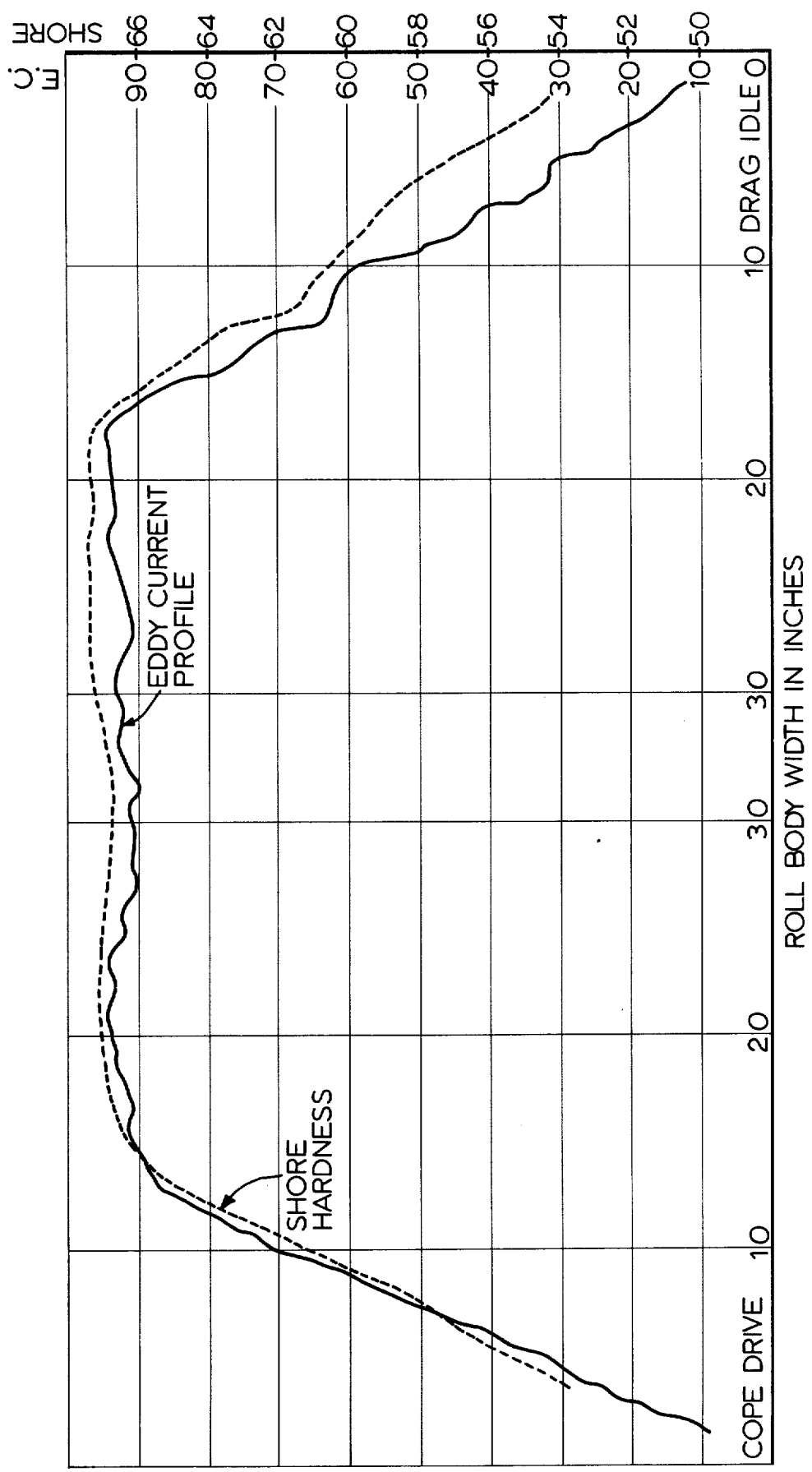
FIG. 3 is a plot across the width of a rolling mill roll comparing shore hardness readings and eddy current readings (magnetic permeability) for a typical rolling mill roll.

I found that in the case of a steel body, such as a rolling-mill roll, the measurement of the magnetic permeability or conductivity of the metal with an eddy current measuring device is a particularly suitable non-destructive testing method for obtaining measurements that can be correlated with the said physical parameters, particularly with the hardness of the material comprising the roll surface. Reference may be made to FIG. 3 of the drawings, which shows clearly the close correlation that is obtainable between eddy current conductivity and hardness, which in this example is shore hardness. Thus, since the chemical composition and the heat treatment of such a roll normally are substantially uniform, it is found as shown by FIG. 3 that eddy current variations can be related directly to hardness. Since however, as explained above, eddy current readings may be affected by other parameters, such as crystal orientation, which do not necessarily foreshadow the possibility of the appearance of defects, differences are always possible. The tests made to date show a correlation of about 95%. It is found moreover that the specific relation between eddy current readings and absolute values of hardness differs from roll to roll and must be established for each roll. Other known methods of measuring magnetic permeability could of course be used, but an eddy current device is particularly preferred for simplicity, accuracy and robustness.

Other forms of non-destructive testing that will give readings correlating with hardness can also be employed in the method of this invention, such as ultrasonic, infra-red examinations of the heated roll, and holographic. Apparatus is also known which will give direct readings of hardness on a meter or recorder, but they generally are not suited for use with rolls since they inherently mark the surface under test, and this is undesirable with the highly polished surfaces of such rolls.

The testing scan shown in FIG. 3 as made by use of the apparatus of FIGS. 1 and 2, was taken along a line parallel to the roll axis, the abscissa being the roll width in inches while the ordinate is the hardness in shore measurement and the eddy current conductivity in arbitrary units. In this particular figure the eddy current scan or profile as produced by the apparatus 42 is shown as a solid line, while the corresponding shore hardness, as measured by direct testing means, is shown as a broken line. The close correspondence between the two measurements is very apparent. The corresponding rate of change of eddy current readings or hardness per linear inch of the roll width is indicated by the slope of the respective profile line. As will be apparent to those skilled in the art the apparatus 42 could be arranged to produce the corresponding plot of rate of change directly by inclusion therein of a suitable differentiation circuit.

The reference line for the measurement could instead be a helix around the roll surface coaxial with the roll axis but since, as described above in the case of a steel rolling mill roll, the predominant parameter to be considered is the hardness and different zones of hardness usually are present in the form of circular bands, a linear plot of the kind illustrated is found in this instance to provide the required information. If desired the plot can be repeated on axial lines spaced around the circumference of the roll.

By way of example, in the case of a typical new steel hot rolling mill back-up roll of the type described above, I found with the testing equipment employed (Automation Industries Model U.M. 1500) operated at a frequency of 5 KH that the possibility of cracking or spalling was sufficiently low for the roll to be acceptable if the rate of change of eddy current readings per linear inch was less than about 10 or 11 per linear inch, though a value of less than 8 was preferred. The hardness and/or eddy current profile of a roll is not static, but changes considerably during its lifetime owing principally to the work hardening during operation. The measurement on a used roll should therefore be made at regular intervals and particularly when the roll has been removed and the surface re-trued to the required rolling shape.

It will be understood that the methods of the invention can only show the level of probability that a particular roll will or will not become defective in normal usage, and there can be no guarantee therefore that any particular roll which gives low rate of change readings will not become defective. With the testing arrangement described above I found that rolls giving a rate of change of eddy current readings of more than 15 per linear inch had a high probability of defects, while those with readings less than 10 had a low probability. These readings can be categorised in more detail as follows:

a. Less than 5 per linear inch. A standard to be obtained if possible with new rolls and an excellent indication that the roll will be satisfactory throughout its life.

b. Between 5 and 8. A good standard for new rolls and an excellent standard for a used roll.

c. Between 8 and 11. A poor standard for a new roll and an acceptable one for a used roll.

d. Between 11 and 14. Completely unacceptable for a new roll and sufficiently unacceptable for a used roll to justify lathe cutting or grinding until more acceptable values have been achieved.

e. Above 14. The probability of spalling is so high that corrective action is essential before further use of the roll.

One special effect which I have noted that may modify the values quoted above (it must again be emphasized that they are obtained with a particular test arrangement) is when a high but otherwise acceptable rate of change is immediately followed by another high rate of change in the opposite direction. Although individually each rate of change may be acceptable their close juxtaposition indicates an undesirable situation for which corrective action should be undertaken.

If rates of change of shore values are to be considered then it can be stated that with rolling mill roll as described a rate of change of less than 2.5 units per linear inch was preferred for a new roll, while 2.5 to 3.6 was considered acceptable for a used roll, and any reading over 3.6 indicated that corrective action was required. These figures cannot be used directly for other surfaces, since the acceptable values will differ substantially with the average hardness; thus a rate of change that is acceptable for a body of average shore hardness 65 may be completely unacceptable if the shore hardness is only about 50.

Figure 4:
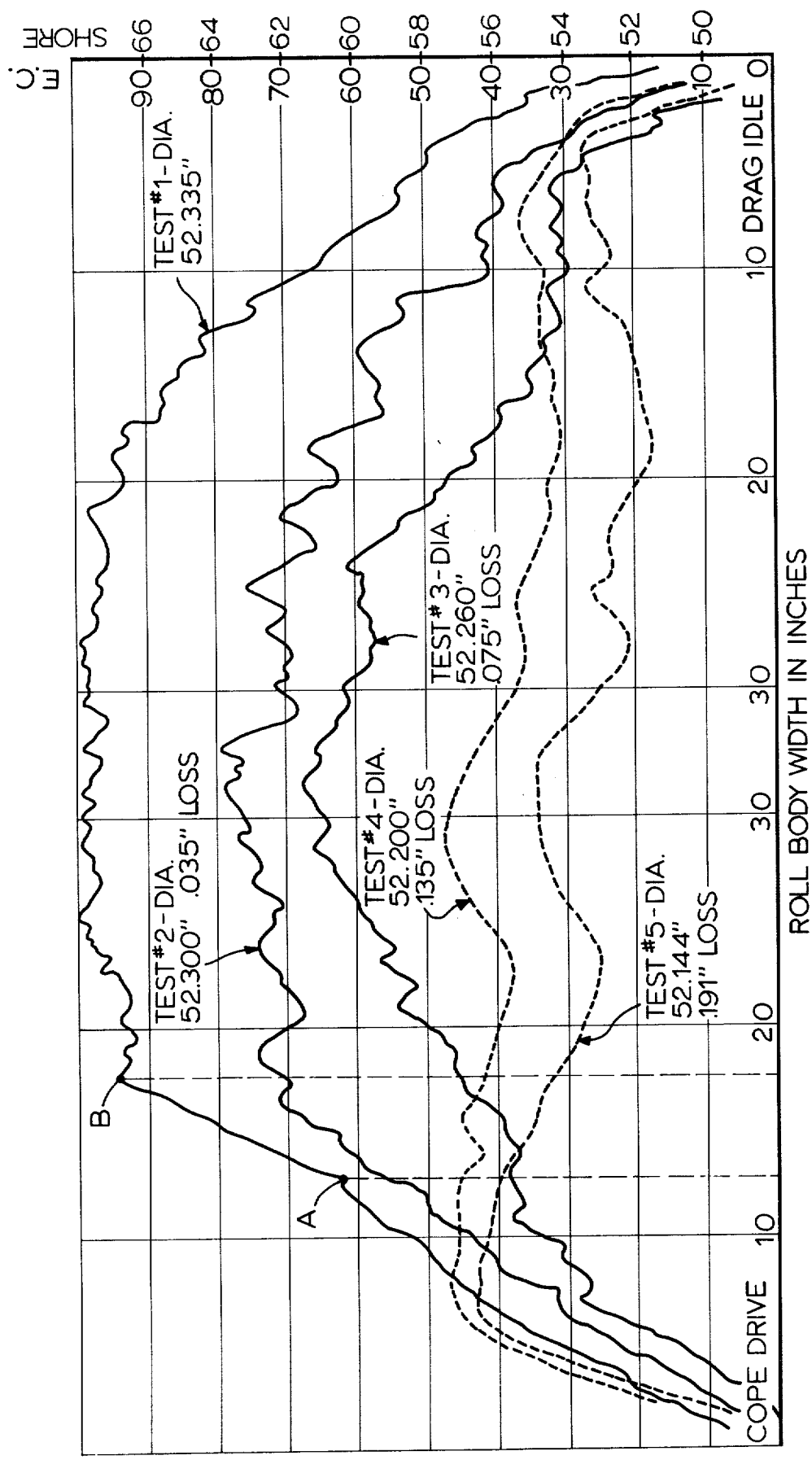
FIG. 4 is a plot across the width of another roll showing the eddy current readings before and during the performance thereon of a mechanical operation consisting of successive removal of layers of the roll periphery.

FIG. 4 illustrates very clearly the effect of work hardening on the peripheral part of a steel roll, and the changes that are obtained by removing the surface layers thereof. Test scan No. 1 was made at a diameter of 52.335 inches and demonstrates a section of most rapid change of eddy current readings between the points A and B, although the actual rate of change is only 5 which is well within the required value for a new roll, let alone a used work-hardened roll. Tests No. 2, 3, and 4 were taken upon removal respectively of 0.035 inch, 0.075 inch and 0.135 inch show a progressive change in characteristic as the work-hardened portion of the roll material is removed, and the roll surface reverts to what was almost certainly its original characteristic. Test No. 5 with 0.191 inch removed is sufficiently similar to test No. 4 to show that there is no point in the removal of further material.

At the present time the preferred mechanical operation performed on the body to reduce the rate of change of hardness to below the required maximum value is cutting or grinding away the outer portion of the body to expose parts thereof having less hardness variation. It has now been found with hot rolling mill back-up rolls that produce a characteristic which indicates the possibility of a defect, that the amount of up to 0.040 inch previously removed by grinding for truing purposes is not sufficient, and an amount of 0.70 ± 0.20 inch should be removed. The removal of this larger amount however compares very favourably with the 2 inches or more that may require removal to eliminate a spall or crack that has actually occurred. Other operations that can be employed are, for example, suitable heat treatments and surface anneals.

Figure 5:
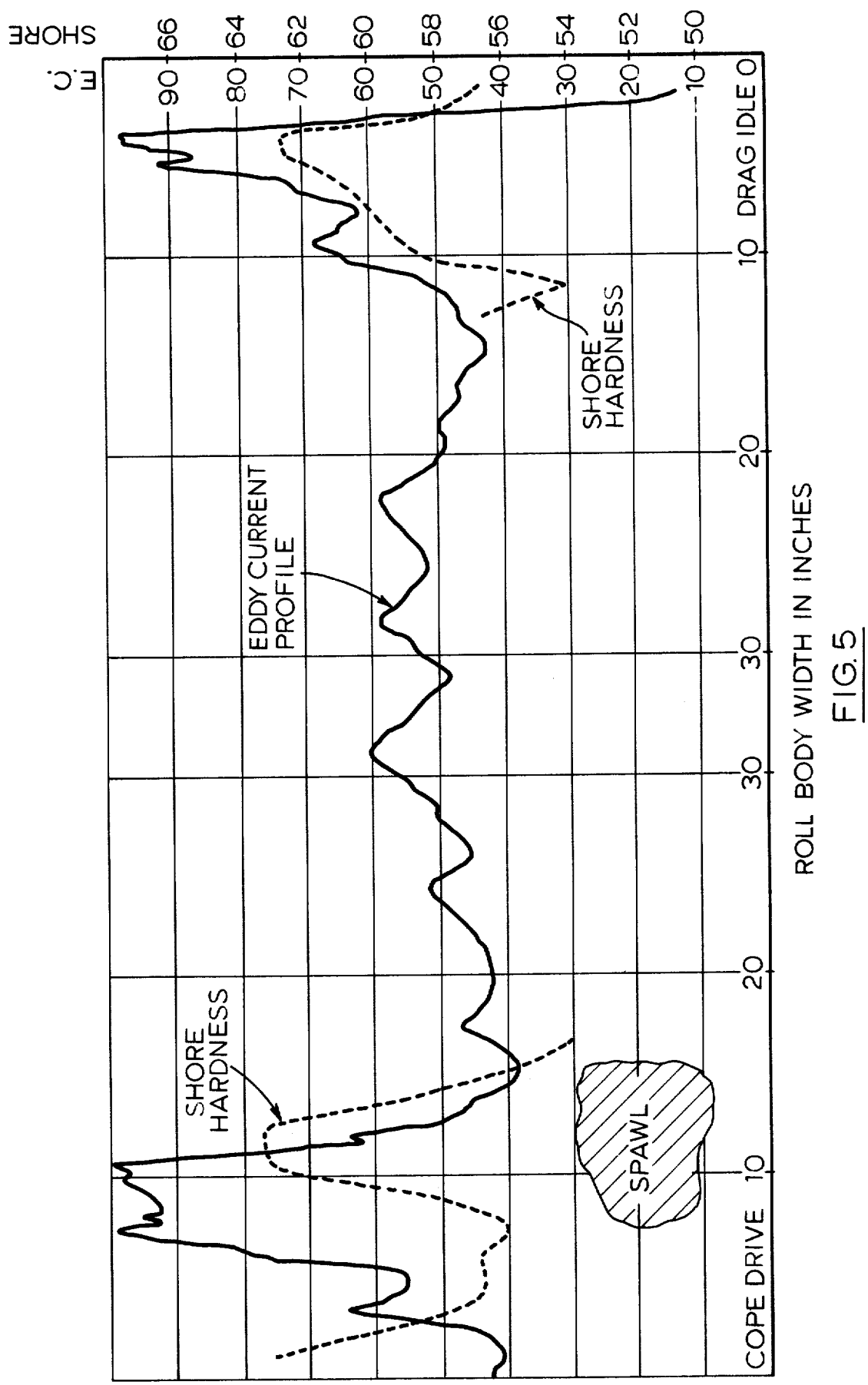
FIG. 5 is another plot similar to FIG. 3 showing the eddy current readings across the respective roll, the shore hardness readings adjacent the ends of the roll, and showing the location of a spawl that developed with this specific roll.
Figure 6:
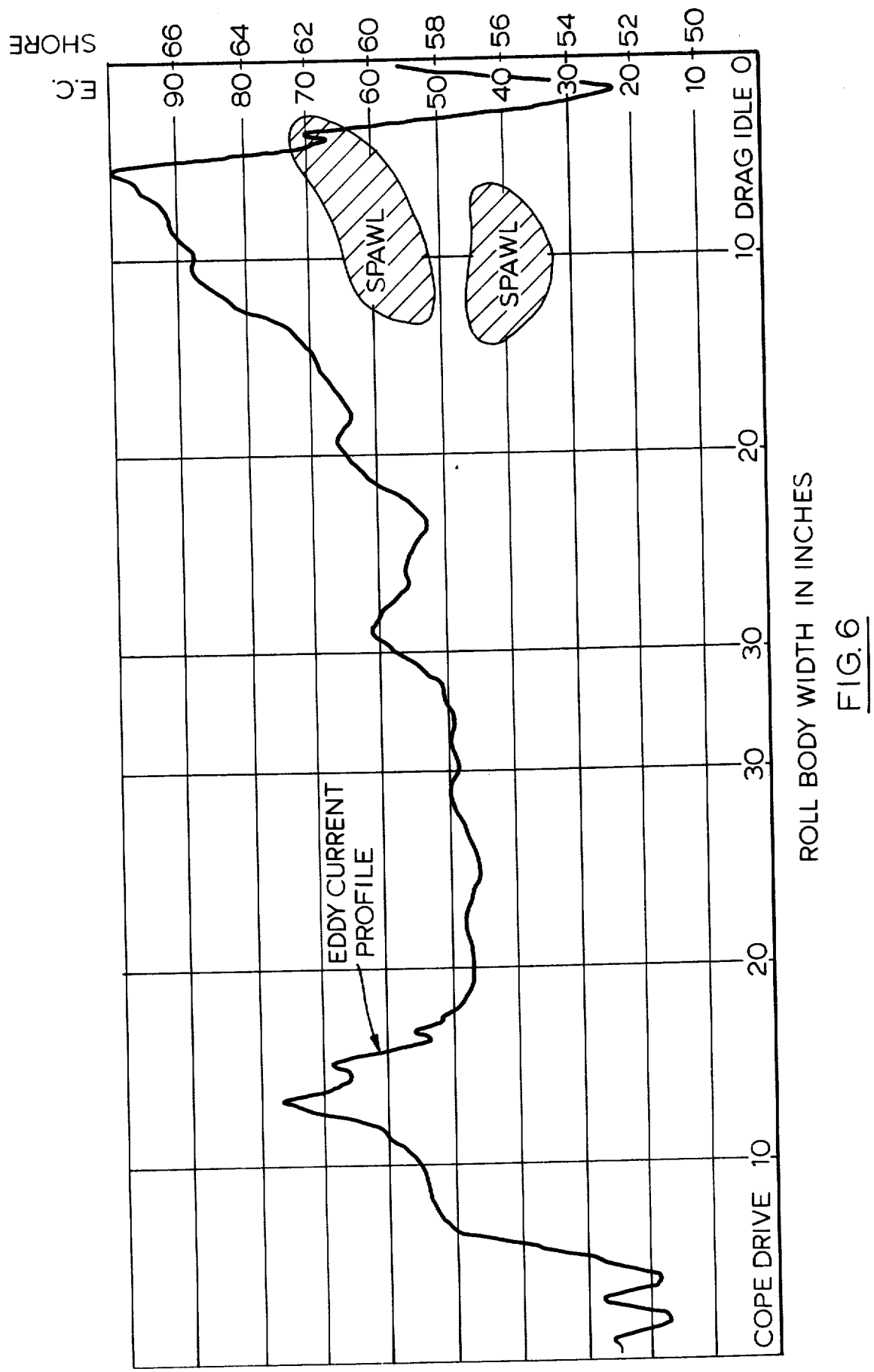
FIG. 6 is a further plot of eddy current readings only taken with a further respective roll, and showing also the location of a spawl that developed with this specific roll.

Reference is now made to FIGS. 5 and 6 which show two graphs obtained with respective rolls that spawled, the locations of the spawls along the axis being indicated to show their location relative to parts of the graphs of high rates of change.

In the graph of FIG. 5 a complete plot of eddy current readings is given but only a partial plot of shore hardness. The spawl is located in the neighbourhood where there is a change of eddy current units of about 26 per inch, the corresponding change of shore hardness units in this instance being about 3.5 per inch. As described above with rolling mill rolls it is the parts thereof adjacent the ends that are subjected to the greatest stresses and most spalls and cracks appear in these parts, so that a hardness and/or eddy current plot confined to the edge parts may give all the information required.

In the graph of FIG. 6 only eddy current units are plotted. It will be noted that two spawls occurred at an axial location at which a rate of change of about 32 units per inch was obtained.

The values of hardness are specified in this specification in terms of Shore values, and the corresponding values in any other system of measurement, such as Vickers and Brinell will be readily apparent to those skilled in the art. Many different tables are available giving rapid conversion from one system to another.

I claim:

1. A method of testing for and at least reducing the possibility of the occurrence of cracking, spalling or like defects in the exterior cylindrical surface of a cylindrical steel rolling mill roll, the method including the steps of:

a. determining the rate of change of hardness along a reference direction for at least a part of the roll surface to find locations therealong having rates of change greater than a predetermined maximum value known to foreshadow the possibility of the occurrence of defects for the roll and the conditions to which it is subjected in operation, and b. when the rate of change of hardness along the reference direction exceeds the said maximum value removing material from the roll including the tested surface until the rate of change of hardness is below another predetermined maximum value.

2. A method as claimed in claim 1, wherein the reference direction is a straight line parallel to the roll axis.

3. A method as claimed in claim 1, wherein the said rate of change of hardness is less than 2.5 units of shore hardness per linear inch.

4. A method as claimed in claim 1, wherein the first-mentioned predetermined rate of change of hardness is about 2.5 units of shore hardness per linear inch, and the said another predetermined maximum value applicable after the removal of the material is about 3.6 units of shore hardness per linear inch.

5. A method as claimed in claim 1, wherein the said removal of material is performed as a series of successive steps, and including the further steps of determining the rate of change of hardness along the reference direction between each two immediately successive steps, and terminating the removal of material when the preceding determination shows that the rate of change of hardness is less than the said another predetermined value.

6. A method of testing for and at least reducing the possibility of the occurrence of cracking, spalling or like defects in the exterior cylindrical surface of a cylindrical steel rolling mill roll, the method including the steps of:

a. determining by means of an eddy current detector the rate of change of magnetic conductivity along a reference direction for at least a part of the roll surface to find locations therealong having rates of change greater than a predetermined maximum value known to foreshadow the possibility of the occurrence of defects for the roll and the conditions to which it is subjected in operation, and b. when the rate of change along the reference direction exceeds the said maximum value removing material from the roll including the tested surface until the rate of change is below another predetermined maximum value.

7. A method as claimed in claim 6, wherein the reference direction is a straight line parallel to the roll axis.

8. A method as claimed in claim 6, wherein the said removal of material is performed as a series of successive steps, and including the further steps of determining the rate of change along the reference direction between each two immediately successive steps, and terminating the removal when the preceding determination shows that the rate of change is less than the said another predetermined value.

9. A method of testing for and at least reducing the possibility of the occurrence of cracking, spalling or like defects in the exterior cylindrical surface of a cylindrical steel rolling mill roll, the method including the steps of:

a. determining the rate of change of hardness along a reference direction for at least a part of the roll surface to find locations therealong having rates of change greater than a predetermined maximum value known to foreshadow the possibility of the occurrence of defects for the roll and the conditions to which it is subjected in operation, and b. when the rate of change of hardness along the reference direction exceeds the said maximum value heat-treating the roll, c. determining the rate of change along the reference direction on the heat-treated roll, and d. repeating the steps b and c as necessary until the rate of change is below another predetermined maximum value.

10. A method as claimed in claim 9, wherein the reference direction is a straight line parallel to the roll axis.

11. A method as claimed in claim 9, wherein the said rate of change of hardness is less than 2.5 units of shore hardness per linear inch.

12. A method of testing for and at least reducing the possibility of the occurrence of cracking, spalling or like defects in the exterior cylindrical surface of a cylindrical steel rolling mill roll, the method including the steps of:

a. determining by means of an eddy current detector the rate of change of magnetic conductivity along a reference direction for at least a part of the roll surface to find locations therealong having rates of change greater than a predetermined maximum value known to foreshadow the possibility of the occurrence of defects for the roll and the conditions to which it is subjected in operation, and b. when the rate of change along the reference direction exceeds the said maximum value heat-treating the roll, c. determining the rate of change along the reference direction on the heat-treated roll, and d. repeating the steps b and c as necessary until the rate of change is below another predetermined maximum value.

13. A method as claimed in claim 12, wherein the reference direction is a straight line parallel to the roll axis.

* * * * *